(12) United States Patent
Ehlert et al.

(10) Patent No.: US 8,459,122 B2
(45) Date of Patent: Jun. 11, 2013

(54) AMPLIFYING ULTRASONIC WAVEGUIDES

(75) Inventors: Thomas David Ehlert, Neenah, WI (US); George Bromfield, Salt Lake City, UT (US); Patrick Sean McNichols, Hortonville, WI (US); Norman R. Stegelmann, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/228,985

(22) Filed: Sep. 9, 2011

(65) Prior Publication Data

US 2011/0314919 A1    Dec. 29, 2011

Related U.S. Application Data

(62) Division of application No. 11/301,118, filed on Dec. 12, 2005, now Pat. No. 8,033,173.

(51) Int. Cl.
*G01N 24/00* (2006.01)
(52) U.S. Cl.
USPC ............................................. 73/644; 73/570
(58) Field of Classification Search
USPC ................. 73/617, 584, 587, 620, 627, 649, 73/644; 367/151, 162, 176
See application file for complete search history.

(56) References Cited

U.S. PATENT DOCUMENTS

| | | | |
|---|---|---|---|
| 4,275,060 A | 6/1981 | Geering | |
| 4,473,769 A * | 9/1984 | Nguyen | 310/334 |
| 4,939,826 A * | 7/1990 | Shoup | 29/25.35 |
| 5,180,363 A | 1/1993 | Idemoto et al. | |
| 5,275,060 A * | 1/1994 | Lynnworth | 73/861.18 |
| 5,297,723 A | 3/1994 | Benn et al. | |
| 5,334,183 A * | 8/1994 | Wuchinich | 606/46 |
| 5,629,906 A * | 5/1997 | Sudol et al. | 367/162 |
| 5,746,756 A * | 5/1998 | Bromfield et al. | 606/169 |
| 5,772,627 A * | 6/1998 | Acosta et al. | 604/22 |
| 5,865,912 A | 2/1999 | Morimoto et al. | |
| 5,936,150 A * | 8/1999 | Kobrin et al. | 73/24.06 |
| 5,971,949 A | 10/1999 | Levin et al. | |
| 6,068,647 A | 5/2000 | Witt et al. | |
| 6,514,895 B1 * | 2/2003 | Chiu et al. | 501/137 |
| 6,547,903 B1 * | 4/2003 | McNichols et al. | 156/64 |
| 6,617,764 B2 * | 9/2003 | Sebastian et al. | 310/329 |
| 6,676,003 B2 | 1/2004 | Ehlert et al. | |

(Continued)

FOREIGN PATENT DOCUMENTS

| EP | 0382975 A1 | 8/1990 |
|---|---|---|
| EP | 0382975 B1 | 11/1995 |

(Continued)

OTHER PUBLICATIONS

"Hot Isostatic Pressing of Metal Powders," ASM Handbooks Online, vol. 7, Powder Metal Technologies and Applications, 2002.*

(Continued)

*Primary Examiner* — Peter Macchiarolo
*Assistant Examiner* — Samir M Shah
(74) *Attorney, Agent, or Firm* — Armstrong Teasdale LLP

(57) ABSTRACT

Ultrasonic waveguides having improved velocity gain are disclosed for use in ultrasonic medical devices. Specifically, the ultrasonic waveguides comprises a first material having a higher acoustic impedance and a second material having a lower acoustic impedance.

19 Claims, 9 Drawing Sheets

U.S. PATENT DOCUMENTS

| | | | |
|---|---|---|---|
| 6,726,698 B2* | 4/2004 | Cimino | 606/169 |
| 6,758,925 B1* | 7/2004 | Stegelmann | 156/73.1 |
| 6,767,420 B2 | 7/2004 | Stegelmann | |
| 6,786,383 B2* | 9/2004 | Stegelmann | 228/1.1 |
| 2002/0043898 A1 | 4/2002 | Sebastian et al. | |
| 2004/0094603 A1 | 5/2004 | Stegelmann | |
| 2004/0176686 A1* | 9/2004 | Hare et al. | 600/431 |
| 2005/0112397 A1 | 5/2005 | Rolfe et al. | |
| 2006/0100616 A1* | 5/2006 | Beaupre | 606/34 |
| 2007/0130771 A1* | 6/2007 | Ehlert et al. | 29/896.2 |
| 2007/0131034 A1* | 6/2007 | Ehlert et al. | 73/617 |
| 2008/0173641 A1* | 7/2008 | Hadidi et al. | 219/690 |
| 2010/0108567 A1* | 5/2010 | Medoff | 208/49 |

FOREIGN PATENT DOCUMENTS

| | | |
|---|---|---|
| JP | 8260003 | 10/1996 |
| JP | 11037981 A | 2/1999 |
| JP | 2002096024 A | 4/2002 |
| WO | 0223145 A2 | 3/2002 |
| WO | 2004060581 A1 | 7/2004 |
| WO | 2004060582 A1 | 7/2004 |
| WO | 2005009489 A2 | 2/2005 |
| WO | 2005009729 A2 | 2/2005 |

OTHER PUBLICATIONS

Office Action issued in EP Patent Application No. 06758964.8 mailed Dec. 3, 2010.

Description of Monel, available at http://www.specialmetals.com/documents/Monel%20alloy%020400.pdf(last visited Jan. 10, 2011).

Non-final Office Action from U.S. Appl. No. 11/301,137 mailed Dec. 18, 2009.

J. J. Conway and F. J. Rizzo, "Hot Isostatic Pressing of Metal Powders," vol. 7, ASM Handbook.

"Alloys: Monel," pp. 417-419.

Wang, et al., "Fabrication of Lead Zirconate Titanate Microrods for 1-3 Piezocomposites Using Hot Isostatic Pressing with Silicon Molds," J. Am. Ceram. Soc., vol. 82(1), pp. 213-215, 1999.

International Search Report from PCT/US2006/015229, dated Aug. 25, 2006.

International Search Report from PCT/US2006/016911, dated Aug. 23, 2006.

Frederick, J., "Ultrasonic Engineering", 1965, pp. 60-74, John Wiley & Sons, Inc., New York, U.S.

European Office Action regarding EP Application No. 06758964.8, dated Jun. 1, 2012.

European Office Action regarding EP Application No. 06751065.1, dated Jul. 6, 2012; 3 pages.

European Office Action regarding EP Application No. 06758964.8, dated Jun. 1, 2012, 4 pages.

Korean Office Action for Patent Application No. 10-2008-7013991, dated Aug. 20, 2012; 7 pages.

Non-final Office action from U.S. Appl. No. 11/301,118 mailed Nov. 12, 2010.

Description of Monel, available at http://www.espi-metals.com/metals/monel.pdf (last visited Mar. 8, 2010).

Korean Office Action for Patent Application No. 10-2008-7013991 dated Feb. 22, 20103; 10 pages.

* cited by examiner

DISTANCE FROM TAIL (mm)

DISTANCE FROM TAIL (mm)

AMPLIFYING ULTRASONIC WAVEGUIDES

CROSS-REFERENCE TO RELATED APPLICATIONS

This application is a divisional application of U.S. patent application Ser. No. 11/301,118, filed on Dec. 12, 2005, which is incorporated in its entirety by reference.

BACKGROUND OF DISCLOSURE

The present disclosure generally relates to improved ultrasonic waveguides. More particularly, the present disclosure relates to ultrasonic waveguides having improved amplification and reduced modal coupling suitable for use in ultrasonic medical devices such as ultrasonic scalpels, phacoemulsifiers, soft tissue aspirators, other ultrasonic surgical tools, and the like.

Many modern surgical procedures involve the use of ultrasonic surgical devices that typically operate at frequencies between 20 kHz and 60 kHz. These devices have application in many surgical specialties including, for example, neurosurgery, general surgery, and ophthalmic surgery. In general, it is known that ultrasonic surgical devices generate ultrasonic frequency vibratory energy that is applied to an ultrasonic applicator that vibrates longitudinally and which contacts the tissues of a patient. The ultrasonic surgical device may, among other surgical effects, cut, fragment, and/or coagulate the contacted tissues of the patient.

Ultrasonic surgical devices are constrained in their ability to generate ultrasonic frequency vibratory energy due to limits inherent in the physical characteristics of the materials typically used to fabricate the devices. For example, titanium alloys are often used for fabrication of the ultrasonic waveguide that is used to contact the tissues of a patient (i.e., ultrasonic applicator). Titanium alloys have inherent fatigue strength and stress limitations that cannot be exceeded or the ultrasonic applicator will crack and/or break resulting in an unusable tool. As a further example, an ultrasonic waveguide, such as for use as an ultrasonic transducer to convert supplied electrical power to ultrasonic frequency vibratory energy, may be fabricated in a stepped-down fashion; that is, geometrically stepping down the diameter of the transducer. While the smaller diameter end of the transducer will typically have a higher amplitude and thus higher tip velocity due to the stepping down, the stepping down leads to considerable stresses at the step, which can result in less efficient transmission of energy, overheating of the transducer, and increased risk of failure.

Additionally, a phenomenon referred to as "modal coupling" can also be responsible for establishing the upper performance boundary of an ultrasonic surgical device. Modal coupling occurs when the vibratory amplitude of an ultrasonic waveguide of an ultrasonic surgical device is increased to such a level that the ultrasonic frequency vibratory energy at the desired resonant frequency is coupled to other modes of vibration, commonly referred to as "parasitic modes". The parasitic modes of vibration may be at lower frequencies, near-by frequencies, or higher frequencies, depending on the design of the system. The parasitic modes of vibration may be longitudinal modes or they may be transverse modes, or they may be more complicated coupled modes. Modal coupling is especially troublesome when the ultrasonic waveguide is an elongate probe or catheter with a length greater than one wavelength at the resonant frequency of the particular ultrasonic surgical device; however, modal coupling may also occur for ultrasonic waveguides shorter than one wavelength and for ultrasonic waveguides that are not shaped like an elongate probe, for example, flat or convex radiating surfaces.

The most common type of modal coupling encountered for ultrasonic surgical devices is the stimulation of a lower or near-by frequency transverse mode so that the ultrasonic waveguide vibrates in the desired longitudinal vibratory mode and an undesired transverse vibratory mode simultaneously. This type of coupled vibration can easily cause stresses in the ultrasonic waveguide material sufficient to break the ultrasonic waveguide.

Ultrasonic surgical devices that operate at high vibratory amplitudes may also generate undesirable heat, primarily in the ultrasonic transducer, but also in the material of other ultrasonic waveguides such as in an ultrasonic applicator, due to internal friction and other losses as the ultrasonic applicator vibrates. If the ultrasonic transducer becomes too hot during a typical procedure, active cooling, such as forced air or water cooling, of the ultrasonic transducer is required, making the ultrasonic surgical handpiece more expensive and more cumbersome due to the additional supply lines. Also, if the ultrasonic applicator becomes too hot, unwanted hot spots or unwanted active zones can result, damaging the tissues of a patient.

Based on the foregoing, there is a need in the art for ultrasonic medical devices and ultrasonic waveguides to be used in ultrasonic medical devices that have good amplification but greatly reduced stresses and heat generation. It would also be desirable for the ultrasonic waveguides to have a reduced risk of modal coupling.

SUMMARY OF THE DISCLOSURE

The present disclosure is directed to novel ultrasonic waveguides that have improved amplification, yet have greatly reduced stresses and heat generation. Additionally, the ultrasonic waveguides have a reduced risk of modal coupling. Generally, the ultrasonic waveguides comprise a component body having a uniform cross-section formed by the process of hot isostatic pressing (HIP) two or more materials. In one embodiment, the improved ultrasonic waveguide comprises a hot isostatically pressed component body. The hot isostatically pressed component body comprises a first material having a higher acoustic impedance and a second material having a lower acoustic impedance. The improved waveguides can be used in ultrasonic medical devices such as ultrasonic scalpels, phacoemulsifiers, soft tissue aspirators, and the like. Additionally, the improved waveguides can be used in other known ultrasonic tools.

As such, the present disclosure is directed to an ultrasonic waveguide comprising a hot isostatically pressed component body. The hot isostatically pressed component body comprises a first material and a second material. The first material has a higher acoustic impedance as compared to the second material.

The present disclosure is further directed to an ultrasonic medical device comprising a one-half wave resonant transducer coupled to a one-half wave ultrasonic waveguide. The one-half wave ultrasonic waveguide comprises a hot isostatically pressed component body comprising a one-quarter wave first material and a one-quarter wave second material. The first material has a higher acoustic impedance as compared to the second material.

The present disclosure is further directed to an ultrasonic waveguide, the ultrasonic waveguide comprising a hot isostatically pressed component body. The hot isostatically pressed component body comprises a first material and a second material. The first material has an acoustic impedance of $40 \times 10^5$ (gm/cm$^2$ sec) or more. The second material has an acoustic impedance of less than $40 \times 10^5$ (gm/cm$^2$ sec).

The present disclosure is further directed to an ultrasonic medical device comprising a one-half wave resonant transducer coupled to a one-half wave ultrasonic waveguide. The one-half wave ultrasonic waveguide comprises a hot isostatically pressed component body comprising a one-quarter wave first material and a one-quarter wave second material. The first material has an acoustic impedance of $40 \times 10^5$ (gm/cm$^2$ sec) or more and the second material has an acoustic impedance of less than $40 \times 10^5$ (gm/cm$^2$ sec).

Other features of the present disclosure will be in part apparent and in part pointed out hereinafter.

DETAILED DESCRIPTION OF THE PREFERRED EMBODIMENT

The present disclosure is generally directed to ultrasonic waveguides having improved amplification and being suitable for use in ultrasonic medical devices. During use, the ultrasonic waveguides of the present disclosure undergo less stress and reduced heat generation than conventional ultrasonic waveguides. Additionally, the phenomenon of modal coupling is less likely to result with the ultrasonic waveguides of the present disclosure, even at increased vibratory amplitudes. As such, when the ultrasonic waveguides as described herein are used in ultrasonic medical devices, the devices are more energy efficient and have a reduced risk of damaging the tissues of the patient.

Ultrasonic waveguides can be used as one or more of the components in an ultrasonic medical device, or other ultrasonic tool. Typically, the ultrasonic waveguides can either provide velocity gain from the ultrasonic transducer to the operative work site (i.e., ultrasonic applicator) or, alternatively, they can be used to transmit ultrasonic energy to remote sites by a series of coupled one-half wave unity gain resonant sections. For example, in one embodiment, the ultrasonic waveguide is a one-half wave ultrasonic waveguide coupled to an ultrasonic resonant transducer to provide velocity gain from the transducer to the work site. In another embodiment, a series of one-half wave ultrasonic waveguides are coupled to each other to transmit ultrasonic energy, such as that used in an ultrasonic scalpel for endoscopic surgical procedures.

Figure 1:
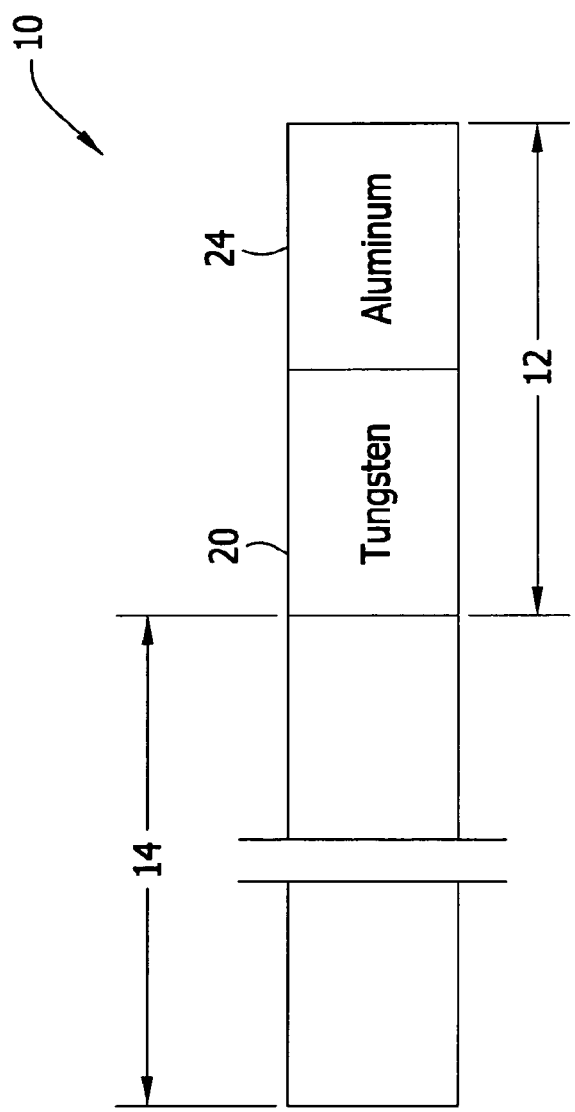
FIG. 1 is a schematic representation of a one-half wave ultrasonic waveguide.

An exemplary ultrasonic assembly 10 including an ultrasonic waveguide 12 coupled to an ultrasonic resonant transducer 14 as described in the disclosure is illustrated schematically in FIG. 1. That is, FIG. 1 illustrates a one-half wave ultrasonic waveguide 12 having a hot isostatically pressed component body with a uniform cross-section area. As depicted in FIG. 1, the hot isostatically pressed component body of this embodiment comprises a proximal one-quarter wave section made of a first material having a high acoustic impedance value 20 and a distal one-quarter wave section made of a second material having a lower acoustic impedance value 24.

Variables such as the diameter, mass, width, thickness, and configuration of the ultrasonic waveguide are not narrowly critical and will depend on the type of ultrasonic medical device or other ultrasonic component in which the ultrasonic waveguide is to be used. The physical variables do determine the particular frequency and amplitude at which the ultrasonic waveguide resonates and vibrates. In particular, the physical variables of an acoustic device, e.g., an ultrasonic waveguide, such as diameter, mass, thickness, overall configuration etc. may be selected such that the waveguide resonates in a desired mode, i.e., a fundamental resonant mode under a given set of conditions, at a particular frequency and with a desired amplitude. For example, it is known that vibration in the desired mode at a desired frequency is achieved by adjusting physical parameters, and it is known that velocity gain, calculated as the ratio of output amplitude to input amplitude, can be adjusted by adjusting physical parameters.

As noted above, the ultrasonic waveguides of the present disclosure have improved amplification, which further produces an improved velocity gain, by employing a first material having a higher acoustic impedance and a second material having a lower acoustic impedance to form the hot isostatically pressed component body. In one specific embodiment, the first material is a metal and the second material is a metal different than the first metal.

The first material has a high acoustic impedance. In one embodiment, the first material has an acoustic impedance of $40 \times 10^5$ (gm/cm$^2$ sec) or more. More suitably, the first material of this embodiment has an acoustic impedance of greater than about $100 \times 10^5$ (gm/cm$^2$ sec).

The first material for use in the hot isostatically pressed component body is suitably selected from the group consisting of copper, gold, iron, molybdenum, MONEL™ (nickel-copper alloy), nickel, platinum, steel, stainless steel, tungsten, and uranium. One particularly preferred first material is tungsten.

The second material for use in the hot isostatically pressed component body suitably has a lower acoustic impedance as compared to the first material. For example, in one embodiment, the second material has an acoustic impedance of less than $40 \times 10^5$ (gm/cm$^2$ sec). Suitable materials for use as the second material include, for example, aluminum, beryllium, brass, cadmium, lead, magnesium, mercury, silver, tin, titanium, and zinc. One particularly preferred second material is aluminum.

As noted above, the ultrasonic waveguides of the present disclosure have improved amplification as compared to conventional ultrasonic waveguides. Generally, ultrasonic amplification can be determined using the theory and equations described in Julian Frederick's "Ultrasonic Engineering", Wiley, 1965. Specifically, the ultrasonic amplification of motion that can be obtained by using two different materials in an ultrasonic waveguide is given by either of the following equations:

$$M = (\rho_1 c_1)/(\rho_2 c_2)$$

or $$M = \sqrt{(E_1 \rho_1 / E_2 \rho_2)}$$

wherein $\rho_1$, $c_1$, and $E_1$ are density, sound velocity (bar) and Young's modulus of one material, and $\rho_2$, $c_2$, and $E_2$ are the corresponding quantities for the other material. The subscripts are assigned to ρc and Eρ so that $\rho_1 c_1 > \rho_2 c_2$ or $E_1\rho_1 > E_2\rho_2$. As such, it is apparent that differences in both the density and Young's modulus, can be utilized to obtain an increase in the displacement or the velocity of one end of an ultrasonic waveguide with respect to the other end.

Since an ultrasonic waveguide that is constructed using two different materials will vibrate with a larger amplitude at the less dense end than it would if both ends were of the same material, amplification can be increased by using a more dense first material and a less dense second material. With this configuration, the ultrasonic waveguide will typically have a higher amplitude and, thus, a higher velocity gain at the end contacting the tissue of the patient.

As noted above, the improved amplification of the ultrasonic waveguides leads to improved velocity gain, which is measured as the ratio of output amplitude to input amplitude. Suitably, the ultrasonic waveguides of the present disclosure are capable of producing a velocity gain of from about 1.5 to about 6.0. More suitably, the ultrasonic waveguides are capable of producing a velocity gain of from about 1.8 to about 5.9, and even more suitably, from about 1.8 to about 4.0.

The ultrasonic waveguides of the present disclosure suitably include a hot isostatically pressed component body characterized by a uniform cross-section area. As a result of this structure, the ultrasonic waveguides have less internal stress as compared to conventional stepped-down-type ultrasonic waveguides. The internal stress of an ultrasonic waveguide can be determined using a commercially available computer modeling program such as Piezo Trans® software (available from PiezoInnovations). Specifically, there is less internal stress at the diffusion bonded joint between the first material and the second material of the ultrasonic waveguides as compared to the internal stress at the step of conventional step waveguides or horns.

Suitably, the ultrasonic waveguides of the present disclosure have an internal stress of less than about 1500 megapascals (Mpa). More suitably, the ultrasonic waveguides of the present disclosure have an internal stress of less than about 1000 Mpa, and even more suitably, less than about 500 Mpa. Preferably, the ultrasonic waveguides of the present disclosure have an internal stress of from about 150 Mpa to about 400 Mpa.

In addition to a uniform cross-section, due to being hot isostatic pressed as described more fully below, the hot isostatically pressed component body of the ultrasonic waveguide has a microstructure characterized by random directional grain alignment and is isotropic in that there is no preferential alignment in any direction or directions, such that the hot isostatically pressed component body uniformly expands and contracts in all radial directions upon excitation at a frequency between about 20 kHz and about 60 kHz. The fact that there is no preferential alignment of grains in any one direction, and that the directional alignment of grains is substantially isotropic and random, yields a hot isostatically pressed component body and, ultimately, an ultrasonic waveguide which expands relatively uniformly in all radial directions, in contrast to forged components which expand relatively non-uniformly in various directions. This more relatively uniform expansion characteristic results in increased uniformity in the work being performed. Specifically, the increased uniformity may prevent unwanted hot spots or unwanted active zones, which can result in damaging the tissues of a patient.

The hot isostatically pressed component body of the present disclosure in certain physical embodiments where mechanical-type work is performed can also be characterized by reduced maintenance requirements in that the uniformity of expansion and contraction can reduce the incidence of wear and deformation on the working surface, because there are not areas of substantially differing impact force.

A further advantage of the waveguides as described herein is that the need for tuning the hot isostatically pressed component body can be eliminated or substantially reduced. In particular, it has been discovered that a HIP-consolidated microstructure has a more consistent resonant operating frequency from component to component than does a forged microstructure. As such, a HIP-consolidated ultrasonic waveguide or other component of a specific predetermined configuration diameter will much more consistently and predictably have a resonant operating frequency of, for example, 20,000 Hz. Accordingly, a 20,000 Hz waveguide or other component can more reliably be produced by simply machining directly to this predetermined configuration, without the need to produce it oversize and gradually machine it to reduce its diameter until the proper frequency is achieved. This is believed to be due to the fact that the HIP-consolidated material has a grain size distribution and grain alignment which does not vary substantially from one component to the next, as does the grain size distribution and grain alignment of forgings.

It has been discovered that HIP-consolidation is especially suited for manufacture of the components of the disclosure because it yields the isotropic microstructure of conventional powder metal sintering, without a sacrifice in density which accompanies sintering; and that it achieves the density of forging, without the non-isotropic microstructure of forging.

A further advantage of the waveguides of the present disclosure is the avoidance of undesired coupling of operating modes which is sometimes present with forged components. In particular, the directional alignment of grains in a forged component results in coupling or linkage of more than one mode of potential expansion and contraction upon excitation. Under certain operating conditions more than one of these modes can be manifested, resulting in non-uniform expansion and contraction. In some instances where a large number of modes are coupled, the component may not even operate, rendering it scrap. Components forged from a highly directional billet, for example, may have as high as a 30% scrap rate. In contrast, the hot isostatically pressed component body of the ultrasonic waveguide of the disclosure operates in only one mode, that being the mode for which it is designed according to acoustical design principles, due to its microstructure being isotropic, such that undesired coupling of more than one operational mode is avoided.

A still further advantage of the waveguides of the present disclosure is that each successive hot isostatically pressed component body has essentially the same microstructure. As such, each one will have essentially the same operational mode, thus lending predictability to the manufacturing process. In contrast, forgings do not have as consistent microstructure from one forging to the next, such that the operation modes, or primary expansion and contraction characteristics, vary from one forging to the next.

As noted above, the ultrasonic waveguides can be used in ultrasonic medical devices. Suitable examples of ultrasonic medical devices comprising the ultrasonic waveguides of the present disclosure can include ultrasonic scalpels, phacoemulsifiers, soft tissue aspirators, other ultrasonic surgical tools, and the like.

Ultrasonic medical devices, such as ultrasonic scalpels, typically comprise multiple ultrasonic waveguides used in series. In one preferred embodiment, the ultrasonic medical device includes a one-half wave resonant transducer coupled with a one-half wave ultrasonic waveguide. The one-half wave ultrasonic waveguide comprises a hot isostatically pressed component body, as described above, comprising a one-quarter wave first material and a one-quarter wave second material. Materials for use as the first material and the second material are described above.

When the ultrasonic medical device includes coupling an ultrasonic waveguide as described herein to another ultrasonic component, such as a resonant transducer, the ultrasonic waveguide can be coupled with the other component using any means known in the art. For example, in one embodiment, the ultrasonic waveguide can be coupled to the transducer by a connector, such as a solid pin or threaded stud. In another embodiment, the ultrasonic waveguide can be coupled to the transducer by a metallurgical fusion zone produced by metallurgically fusing the components together. As discussed more fully below, in one embodiment, the fusion zone can be produced by hot isostatic pressing.

As with the ultrasonic waveguide described above, the ultrasonic medical device including the ultrasonic waveguide of the present disclosure has both an improved amplification and velocity gain and a reduced internal stress as determined using the methods described above. Specifically, the ultrasonic medical device produces a velocity gain of from about 1.5 to about 6.0, more suitably, a velocity gain of from about 1.8 to about 5.9, and even more suitably, from about 1.8 to about 4.0. Additionally, the ultrasonic medical devices have an internal stress of less than about 1500 Mpa. More suitably, the ultrasonic medical devices of the present disclosure have an internal stress of less than about 1000 Mpa, and even more suitably, less than about 500 Mpa. Preferably, the ultrasonic medical device has an internal stress of from about 150 Mpa to about 400 Mpa.

Additionally, the present disclosure is directed to methods of manufacturing the ultrasonic waveguides and ultrasonic medical devices described herein above. For example, in one embodiment, the method for manufacturing an ultrasonic waveguide of the present disclosure includes the following steps: (1) filling an ultrasonic waveguide preform with a first material having an acoustic impedance of $40 \times 10^5$ (gm/cm$^2$ sec) or more and a second material having an acoustic impedance of less than $40 \times 10^5$ (gm/cm$^2$ sec); and (2) hot isostatic pressing the ultrasonic waveguide preform to consolidate the first material and the second material to form a hot isostatically pressed component body.

As noted above, the first step in the method for manufacturing an ultrasonic waveguide includes filling an ultrasonic waveguide preform with a first material and a second material. The first material and the second material can be used in powder form, slug form, solid form, or combinations thereof to produce the ultrasonic waveguide preform. The first and second materials can be added into the preform by any method known in the art. In one embodiment, the ultrasonic waveguide preform is filled with the first material and the second material, each in slug form.

In one embodiment, when filling the ultrasonic waveguide preform with the first and second materials, the first material is added and then the second material is added to the preform. In another embodiment, the second material is added and then the first material is added to the preform.

Typically, the ultrasonic waveguide preform is manufactured larger than needed and is then machined down to the desired size. The ultrasonic waveguide preform is machined down using any method known in the art. Suitably, the preform is machined down to a one-half wave length dimension.

After filling the ultrasonic waveguide preform with the first and second materials, the preform is hot isostatic pressed to consolidate the first material and the second material to form a hot isostatically pressed component body. The method of hot isostatic pressing is well known in the art of ultrasonic horns, such as horns used for bonding two thermoplastic sheets of materials together in the manufacture of personal care products such as diapers. As noted above, the present disclosure uses the method of hot isostatic pressing to produce a hot isostatically pressed component body of an ultrasonic waveguide for use in ultrasonic medical devices.

One suitable method of producing the hot isostatically pressed component body includes employing a pressure vessel which can be pressurized employing a gas, such as argon, of commercial quality to apply a pressure equally over the entire surface area of the hot isostatically pressed component body. The pressure, in combination with the elevated temperature employed, effects consolidation of the materials to a density of at least about 95%, at least about 99%, and even about 100% of the theoretical density of the materials. With this density, the hot isostatically pressed component body has a microstructure that is substantially totally void free. As used herein, the term "substantially void free" refers to a microstructure being 95% free of voids or gaps. Suitably, a microstructure that is substantially void free is 98% free of voids or gaps, more suitably, 99% free of voids, and even more suitably, 100% free of voids.

As the hot isostatically pressed component body is substantially void free, the hot isostatically pressed component body is more resistant to contamination by micro-organisms such as prions. This is especially preferable when working in the medical field such as with ultrasonic medical devices.

For the hot isostatic pressing, a pressure suitable for use in this operation can be, for example, from about 14 ksi to about 16 ksi. More suitably, the pressure for use in hot isostatic pressing of the preform is about 16 ksi. The temperature employed in this operation can be in the range of about 1400° F. (about 760° C.) to about 1600° F. (about 870° C.). The duration of the hot isostatic pressing step depends upon the temperature and pressure selected. As a general proposition, when the pressure is 16 ksi and the temperature is in the range of about 1400° F. (about 760° C.) to about 1600° F. (about 870° C.), the process may employ a time period of about 1.5 hours to about 3 hours, for example 2 hours, in one embodiment. At the conclusion of the hot isostatic pressing step, the component body is held in the hot isostatic pressing pressure vessel and allowed to cool to ambient temperature (about 23.7° C.) and is then removed from the pressure vessel.

The hot isostatically pressed component body is then optionally subjected to final machining operations to impart the desired shape and surface characteristics of the ultrasonic waveguide as described above.

Once the ultrasonic waveguide is manufactured, the ultrasonic waveguide can be utilized to manufacture an ultrasonic medical device. For example, in one embodiment, the present disclosure is directed to a method of manufacturing an ultrasonic medical device by coupling the one-half wave ultrasonic waveguide as manufactured above to a one-half wave resonant transducer.

A suitable resonant transducer may be produced by any means in the art. Alternatively, the resonant transducer may be obtained commercially from Zevex, Inc. (Salt Lake City, Utah).

Figure 3:
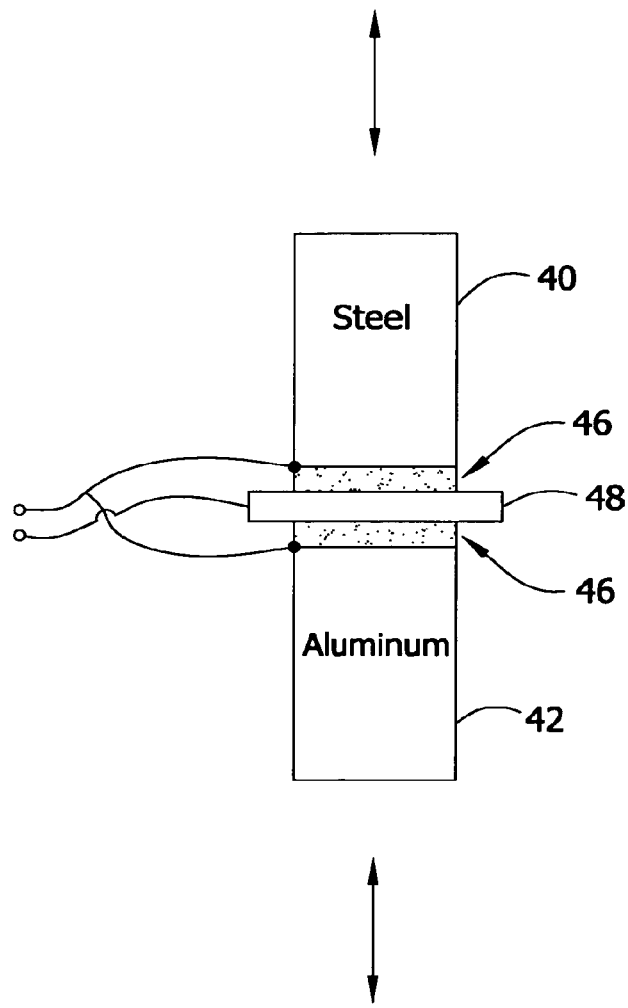
FIG. 3 is a schematic representation of a one-half wave resonant transducer.

In one embodiment, the resonant transducer is a composite transducer, constructed as shown in FIG. 3, which comprises a first material 40, a second material 42 and a piezoelectric crystal 46. Materials for use as the first and second materials of the composite transducer are the same as those described above for use in an ultrasonic waveguide. In one embodiment, the transducer may be further mounted in a fixture or in a protective case by means of the nodal mounting plate 48.

As noted above, any method of coupling ultrasonic components can be used to couple the one-half wave ultrasonic waveguide to the one-half wave resonant transducer. In one embodiment, the one-half wave ultrasonic waveguide is coupled to the one-half wave resonant transducer using a mechanical connector. Suitable connectors for use in coupling the components can include, for example, solid pins, threaded studs, and any combination thereof. One suitable embodiment comprises using a solid pin having a clearance of 0.001 inch or less to provide an interference fit between the components as the connector. In another preferred embodiment, the connector may be partially or fully threaded studs passing through the interfaces. The connectors of any type may be formed from the same materials as the components.

Figure 2:
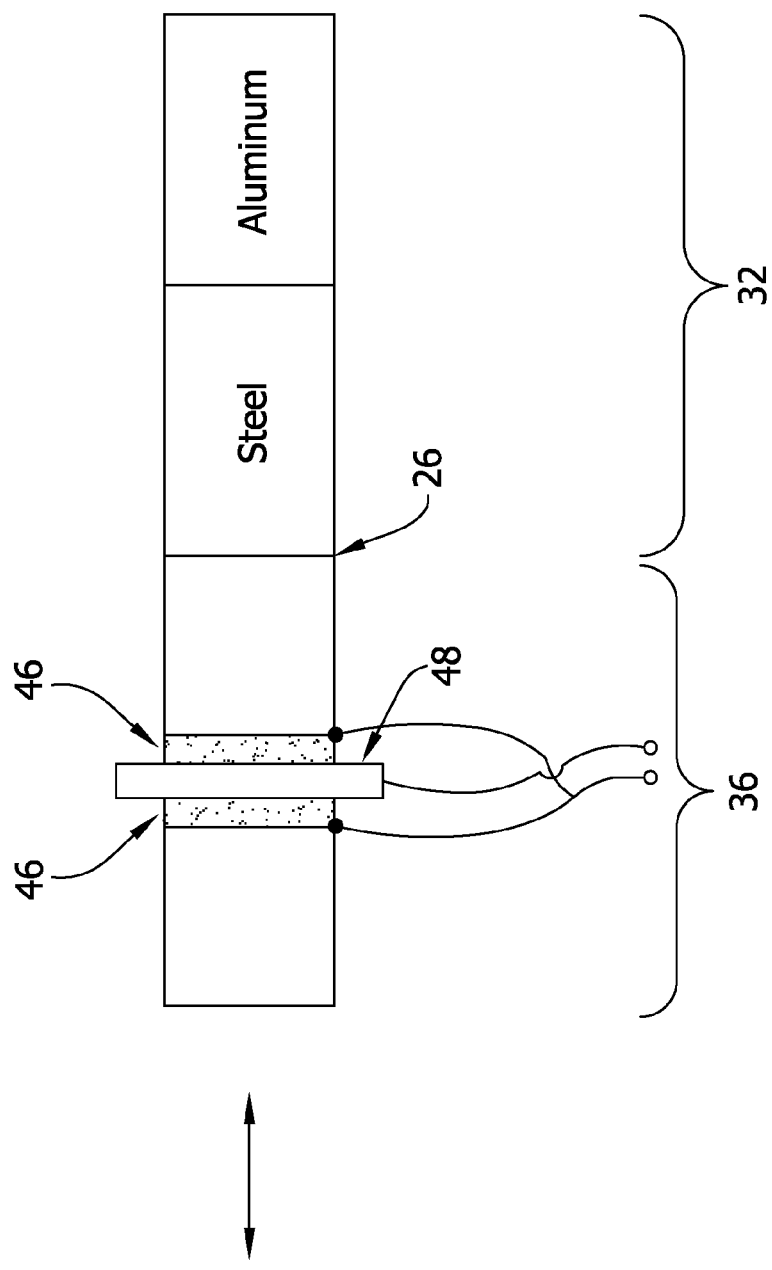
FIG. 2 is a schematic representation of a one-half wave ultrasonic waveguide coupled to a one-half wave resonant transducer.

In another embodiment, the one-half wave ultrasonic waveguide is coupled to the one-half wave resonant transducer by metallurgical fusion, which creates a fusion zone on the interface of the ultrasonic waveguide and resonant transducer. As shown in FIG. 2, the interface 26 is the location of engagement of the energy transfer face of the ultrasonic waveguide 32 to the energy transfer face of the resonant transducer 36. The transfer faces are lapped to be flattened to within two millionths of an inch and thoroughly cleaned with acetone prior to assembly.

Suitably, the fusion zone created by metallurgical fusing the components facilitates more efficient ultrasonic energy transfer between the respective components because it serves to integrate the components to each other, thus eliminating loss of energy between the components at the transfer interface. Moreover, the fusion zone eliminates the need for periodic disassembly to remove wear and oxide on the respective transfer faces of the waveguide and transducer.

In one preferred embodiment, hot isostatic pressing forms these fusion zones. The ultrasonic waveguide and resonant transducer are subjected to hot isostatic pressing in a single pressing operation for the entire assembly. Typically during the hot isostatic pressing step, a high-strength uniform metallurgical diffusion bond is formed between the transfer faces. The resultant metallic fusion formed is characterized as not appreciably indicating a line of demarcation between the components, but rather a uniform transformation of grain structure characteristic of an integral assembly. In one embodiment, the fusion zone can extend from on the order of 0.001 inch (0.0025 cm) into each component to on the order of several thousandths of an inch, such as 0.005 inch (0.0075 cm) into each component, for a total fusion zone width of between about 0.002 inch (0.005 cm) and about 0.01 inch (0.025 cm). In other embodiments, the fusion zone may be wider or narrower.

To prepare the coupled components for the fusion procedure such as hot isostatic pressing, it is first suitable, but not required, to subject seams at the interfaces to a preliminary sealing operation to bring the transfer faces into more intimate contact and to seal the interfaces from external air or atmosphere during hot isostatic pressing. In one embodiment, this is accomplished by electron beam welding as is well understood in the metals joining art, involving a vacuum process to remove any residual air from between the components at their interface, followed by electron beam welding to seal the hairline interface along the exposed outside of the interfaces. By sealing this interface under vacuum conditions, all air or atmosphere is prevented from interfering with subsequent fusion by hot isostatic pressing.

One suitable method of hot isostatic pressing of the components can be carried out similar to the hot isostatic pressing of the first material and second material of the ultrasonic waveguide as described above. Specifically, the components can be hot isostatic pressed by employing a pressure vessel which can be pressurized employing gas, such as argon, of commercial quality to apply a pressure equally over the entire surface area of the assembly. The pressure, in combination with the elevated temperature employed, affects a 100% fusion bonding across the interfaces causing them to become totally integrated to an interface density approaching 100% theoretical density. A pressure suitable for use in this operation range can be, for example, about 16 ksi. The temperature employed in this operation can be in the range of about 1500° F. (815° C.) to about 1600° F. (870° C.) The duration of the hot isostatic pressing step depends upon the temperature and pressure selected. As a general proposition, when the pressure is 16 ksi and the temperature is in the range of about 1500° F. (815° C.) to about 1600° F. (870° C.), the process may employ a time period of from about 1.5 hours to about 3 hours, for example 2 hours, in one embodiment. At the conclusion of the hot isostatic pressing step, the assembly is cooled and removed from the pressure vessel.

EXAMPLE

The following example is simply intended to further illustrate and explain the present disclosure.

The disclosure, therefore, should not be limited to any of the details in this example.

Example 1

In this Example, a one-half wave ultrasonic waveguide comprising a hot isostatically pressed component body comprising one-quarter wave tungsten and one-quarter wave aluminum was produced. This one-half wave ultrasonic waveguide was then coupled to a commercially available resonant transducer (available from Zevex, Inc. (Salt Lake City, Utah)) to produce an ultrasonic assembly. The velocity gain and internal stress of this ultrasonic assembly was then evaluated and compared to the velocity gain and internal stress of a one wave conventional stepped horn assembly made from a one-half wave ultrasonic waveguide of tungsten and a conventional resonant transducer and the velocity gain and internal stress of a one-half wave tungsten waveguide/one-half wave resonant transducer assembly. The conventional stepped horn assembly was made using tungsten in a conventional stepped horn process to form the one-half waveguide of tungsten and connecting the one-half waveguide of tungsten with a resonant transducer (available from Zevex, Inc. (Salt Lake City, Utah)) using a threaded stud. The one-half wave tungsten waveguide/one-half wave resonant transducer assembly was made by filling an ultrasonic waveguide preform with tungsten and then subjecting the preform to a conventional hot isostactic pressing process. The one-half wave tungsten waveguide was then connected to the commercially available resonant transducer (available from Zevex, Inc. (Salt Lake City, Utah)) using a threaded stud.

To produce the one-half wave ultrasonic waveguide comprising a hot isostatically pressed component body, a tungsten slug (such as available from Alfa Aesar, Ward Hill, Mass.) having an acoustic impedance of $101.0 \times 10^5$ (gm/cm$^2$ sec) was introduced into an ultrasonic waveguide preform (commercially available from Bodycote, Andover, Mass.) and then an aluminum slug (such as available from JLO Metal Products, Inc., Chicago, Ill.) having an acoustic impedance of $17.0 \times 10^5$ (gm/cm$^2$ sec) was introduced into the ultrasonic waveguide preform. The ultrasonic waveguide preform was then hot isostatic pressed using a conventional hot isostatic pressing process to form a hot isostatically pressed component body having about 100% density.

The tungsten-aluminum one-half wave ultrasonic waveguide was then machined to the desired size and coupled to a conventional one-half wave resonant transducer comprised of steel and aluminum using a threaded stud.

Physical characteristics, such as diameter and length of the tungsten-aluminum ultrasonic assembly, stepped tungsten horn assembly, and tungsten waveguide/transducer assembly were substantially the same. Additionally, the transducer of the assemblies were set to operate at a frequency of 40 kHz.

The amplification of the three assemblies were then determined at 40 kHz. The amplification of the tungsten-aluminum ultrasonic assembly was determined using the formula set forth above in the specification. Specifically, the amplification of the tungsten-aluminum ultrasonic assembly is equal to the product of the density and sound velocity of tungsten divided by the product of the density and sound velocity of aluminum. The amplification of the stepped tungsten horn assembly was determined using the formula:

$$\text{Amplification} = \frac{\text{larger diameter}}{\text{smaller diameter}}$$

The amplification of the tungsten waveguide/transducer assembly was determined using a Laser Vibrometer (commercially available from Polytec PI, Inc., Auburn, Mass.).

In addition to the amplification, the velocity gain during operation of each of the tungsten-aluminum ultrasonic assembly, stepped tungsten horn assembly, and tungsten waveguide/transducer assembly were then determined by measuring the displacement of output amplitude to input amplitude at the diffusion bond joint or step between the one-quarter wave component nearest to the resonant transducer and the one-quarter wave component farthest from the resonant transducer. The velocity gains of each of the assemblies were then compared. The results are shown in FIGS. 4A-C.

Figure 4A:
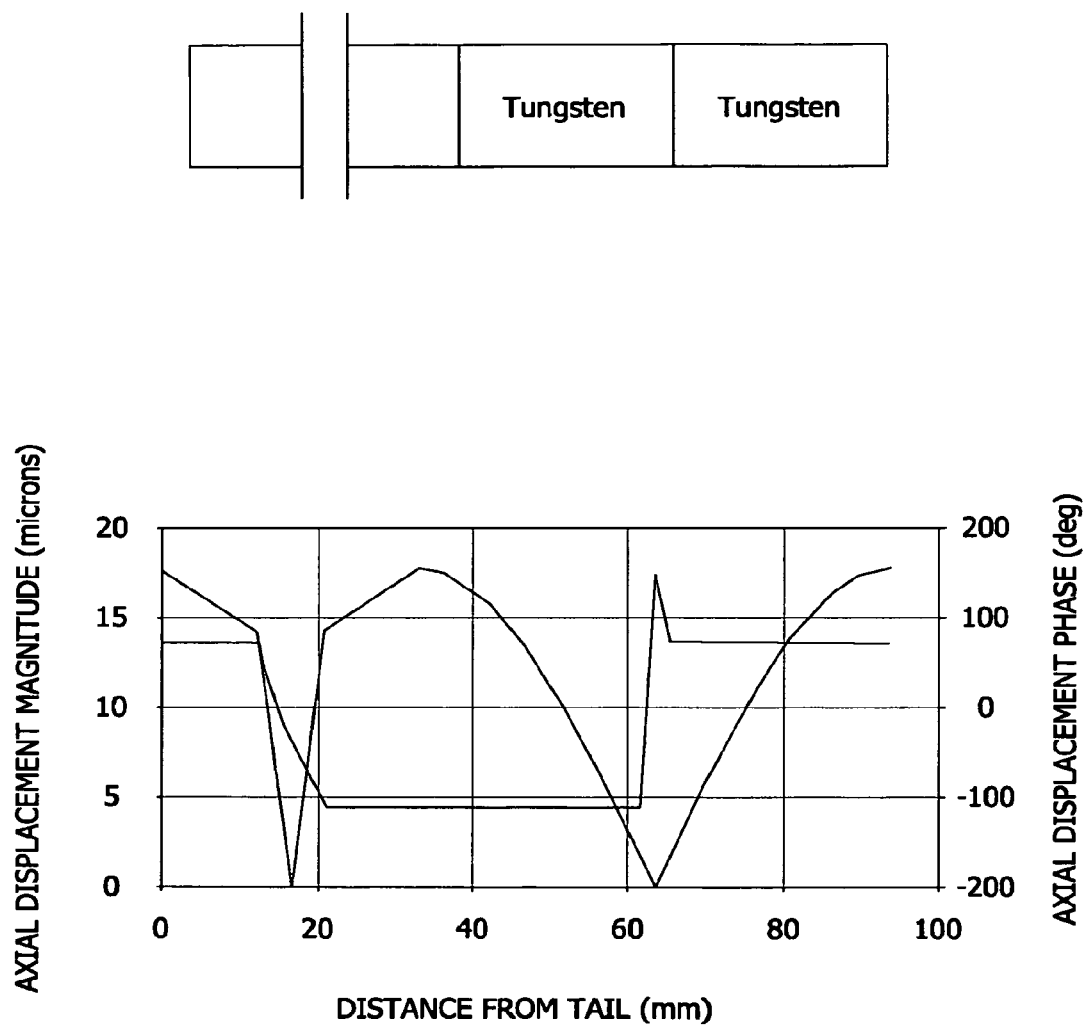
FIGS. 4A-C are graphs depicting the displacement at the diffusion bond of the ultrasonic assembly of the present invention as compared to the displacement at the step of a conventional stepped horn and the displacement at the diffusion bond of a conventional waveguide coupled to a transducer.
Figure 4B:
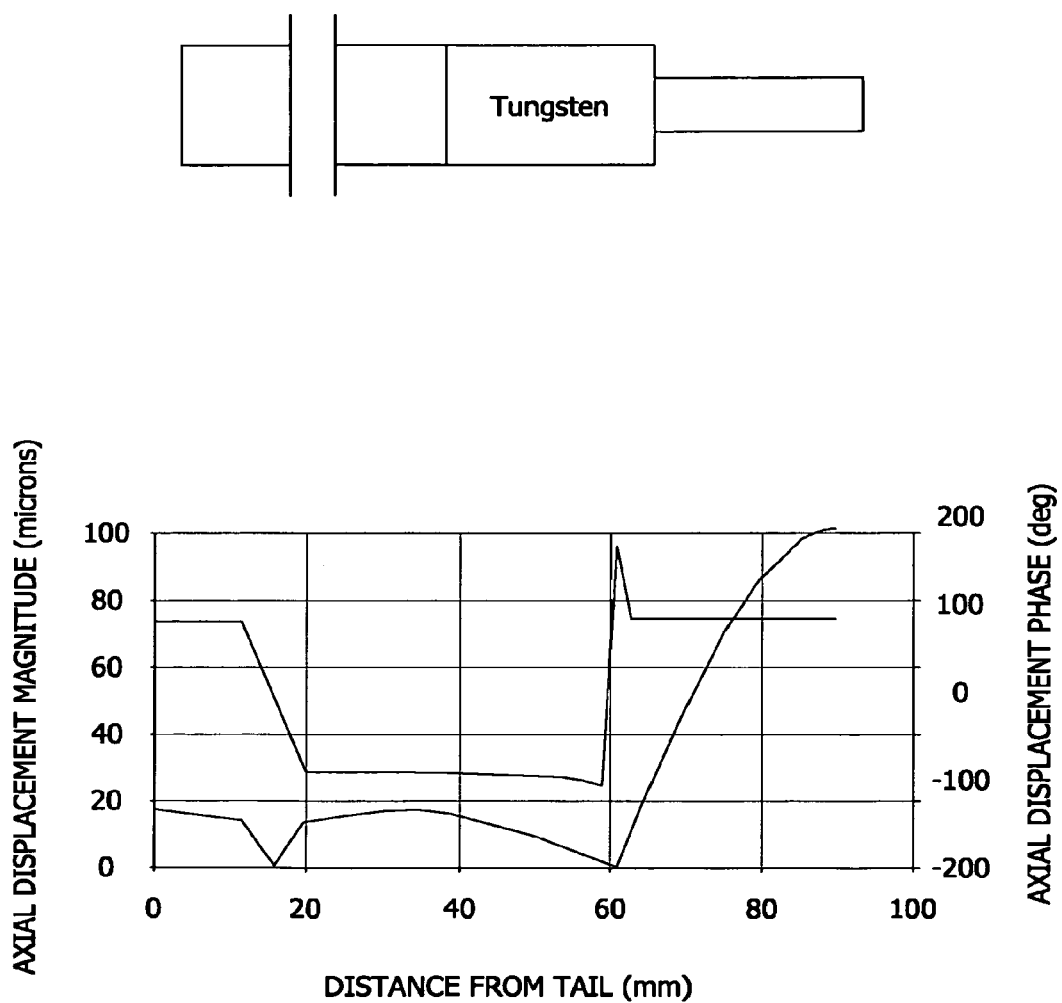
Figure 4C:
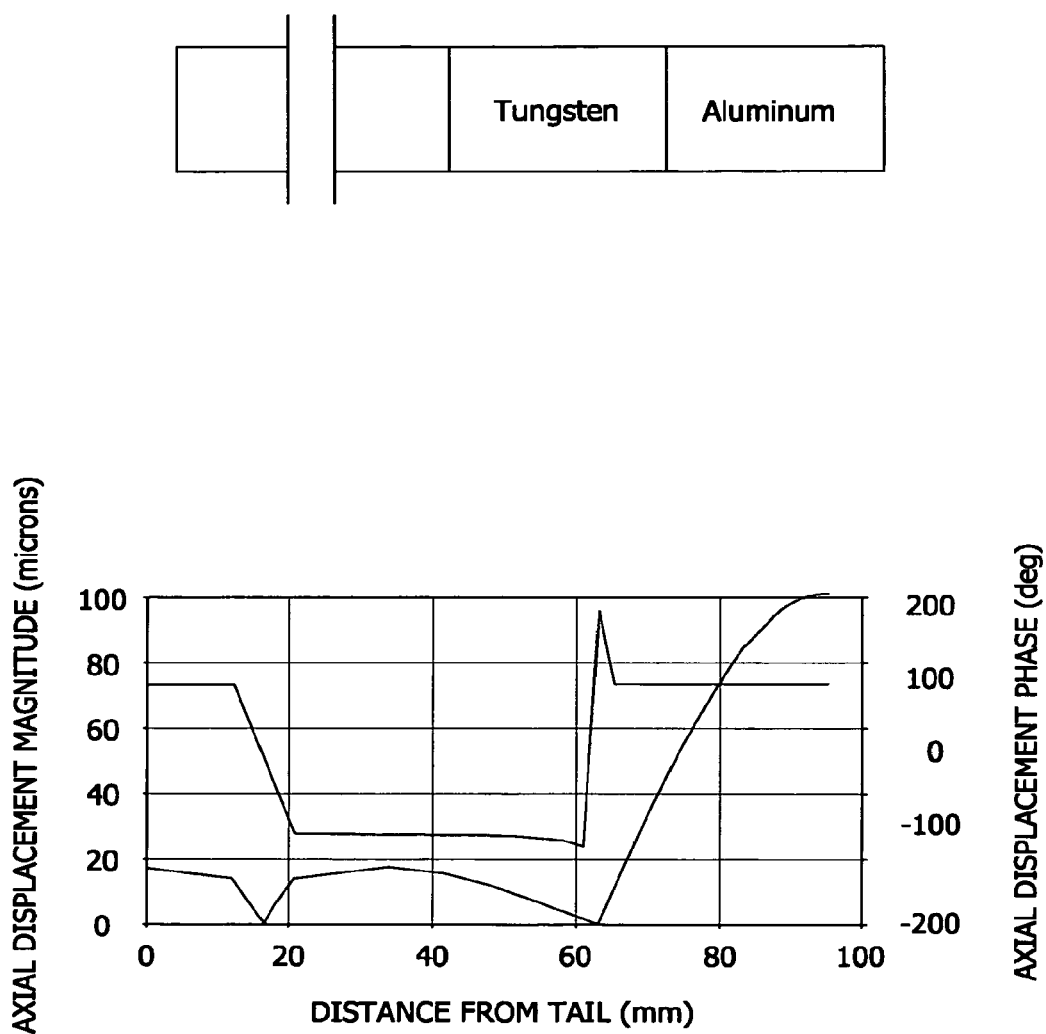

As shown in FIGS. 4A-4C, the displacement at the diffusion bond of the tungsten-aluminum ultrasonic assembly was substantially the same as the displacement at the step of the stepped tungsten horn assembly. As such, the tungsten-aluminum ultrasonic assembly had the same velocity gain as the stepped tungsten horn assembly. The tungsten waveguide/transducer assembly, however, had a much lower velocity gain. Specifically, the displacement at the diffusion bond joint of the tungsten waveguide/transducer assembly was approximately 17.5 microns, while the displacement at the diffusion bond joint of the ultrasonic assembly was approximately 100 microns.

The internal stresses at each of the diffusion bonded joints of the tungsten-aluminum ultrasonic assembly and of the tungsten waveguide/transducer assembly and the internal stress at the step of the stepped tungsten horn assembly were then determined using Piezo Trans® software (available from PiezoInnovations). The results are shown in FIGS. 5A-C.

Figure 5A:
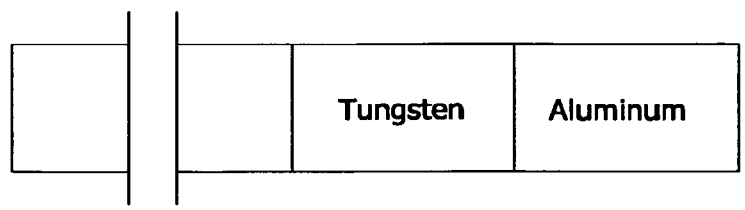
FIGS. 5A-C are graphs depicting the internal stress of the ultrasonic assembly of the present invention as compared to the internal stresses of a conventional stepped horn and a conventional waveguide coupled to a transducer.
Figure 5A:
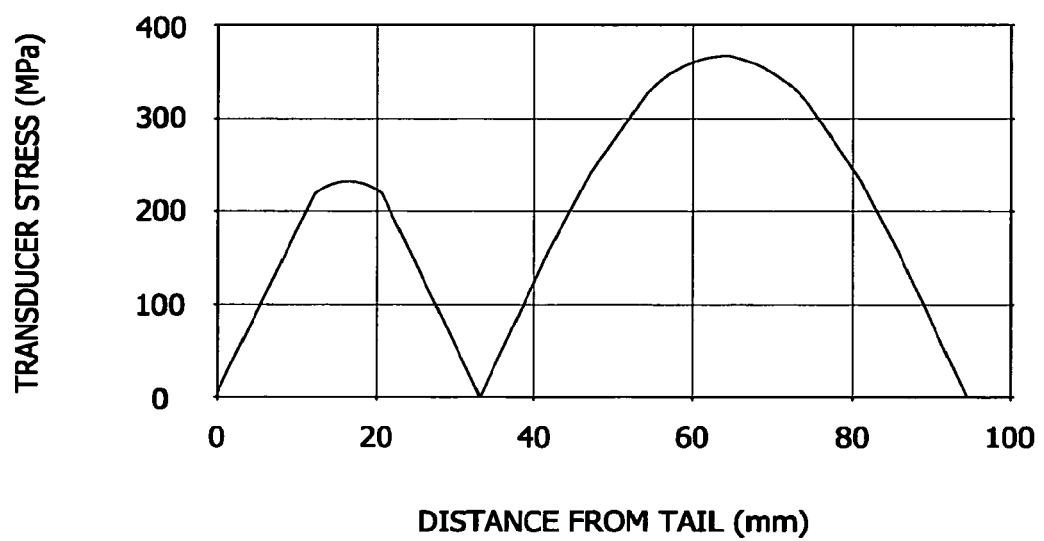
Figure 5B:
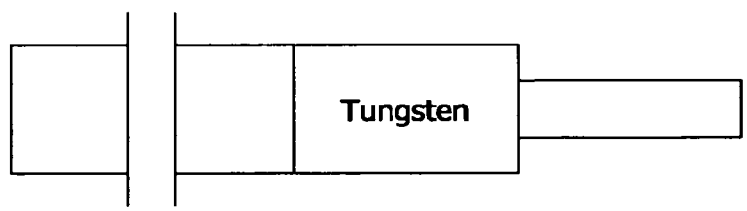
Figure 5B:
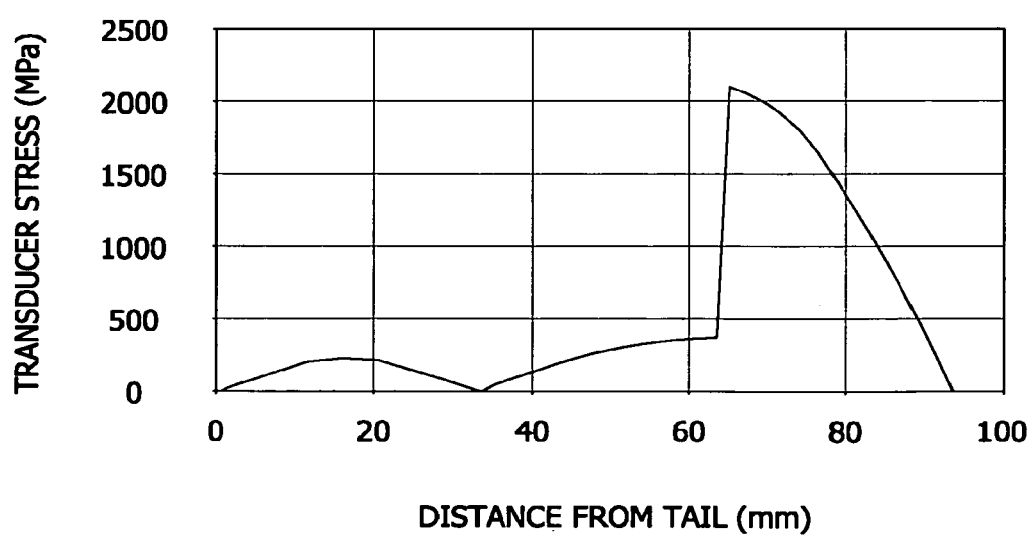
Figure 5C:
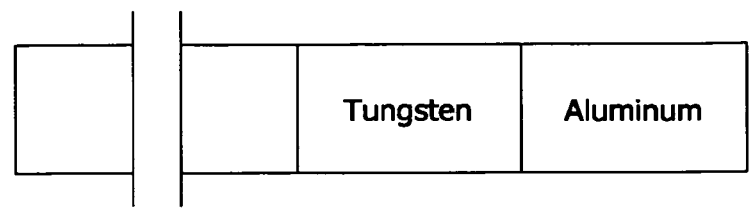
Figure 5C:
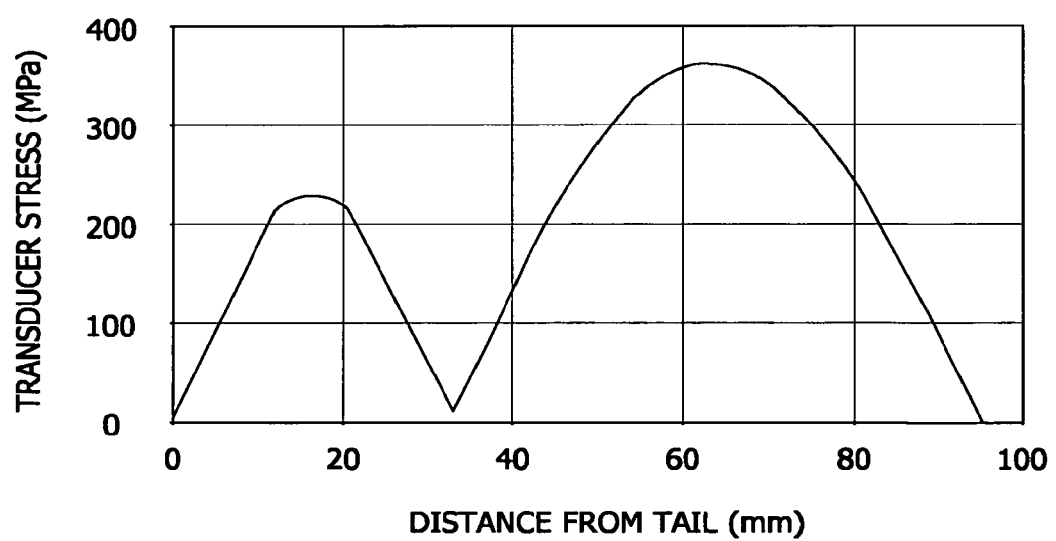

As shown in FIGS. 5A-C, the internal stress at the diffusion bonded joint between the one-quarter wave tungsten and one-quarter wave aluminum of the tungsten-aluminum ultrasonic assembly was approximately 360 MPa. The internal stress at the diffusion bonded joint between the tungsten waveguide and transducer of the tungsten waveguide/transducer assembly was also approximately 360 MPa. The internal stress on the step of the stepped tungsten horn assembly, however, was approximately 2100 MPa. As such, due to the hot isostatic pressing-consolidation of the two materials in a preform having a uniform cross-section, the internal stresses put on the tungsten-aluminum ultrasonic assembly was almost six times less than the internal stress on the step of the stepped tungsten horn assembly, even with the same velocity gain.

In summary, using two different materials, having different acoustic impedances, for the one-quarter wave components provides an ultrasonic assembly providing an improved velocity gain, such as can be produced by a conventional stepped horn assembly, but without the disadvantage of putting high internal stress on the assembly at the step.

In view of the above, it will be seen that the several objects of the disclosure are achieved and other advantageous results obtained.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the disclosure, it is intended that all matter contained in the above description and shown in the accompanying drawings shall be interpreted as illustrative and not in a limiting sense.

What is claimed is:

1. An ultrasonic waveguide comprising a hot isostatically pressed component body comprising a first material and a second material, the first material having an acoustic impedance of $40 \times 10^5$ (gm/cm$^2$ sec) or more, and the second material having an acoustic impedance of less than $40 \times 10^5$ (gm/cm$^2$ sec), wherein the entire hot isostatically pressed component body has a substantially uniform cross-section.

2. The ultrasonic waveguide as set forth in claim 1 wherein the first material is a metal and the second material is a metal.

3. The ultrasonic waveguide as set forth in claim 1 wherein the first material has an acoustic impedance of greater than about $100 \times 10^5$ (gm/cm$^2$ sec).

4. The ultrasonic waveguide as set forth in claim 1 wherein the first material is selected from the group consisting of copper, gold, iron, molybdenum, (nickel-copper alloy), nickel, platinum, steel, stainless steel, tungsten, and uranium.

5. The ultrasonic waveguide as set forth in claim 1 wherein the first material is tungsten.

6. The ultrasonic waveguide as set forth in claim 1 wherein the second material has an acoustic impedance of less than $25 \times 10^5$ (gm/cm$^2$ sec).

7. The ultrasonic waveguide as set forth in claim 1 wherein the second material is selected from the group consisting of aluminum, beryllium, brass, cadmium, lead, magnesium, mercury, silver, tin, titanium, and zinc.

8. The ultrasonic waveguide as set forth in claim 1 wherein the second material is aluminum.

9. The ultrasonic waveguide as set forth in claim 1 being capable of producing a velocity gain of from about 1.5 to about 6.0.

10. The ultrasonic waveguide as set forth in claim 1 having an internal stress of less than about 1500 MPa.

11. The ultrasonic waveguide as set forth in claim 1 wherein the hot isostatically pressed component body comprises a microstructure characterized by isotropically random directional grain alignment.

12. The ultrasonic waveguide as set forth in claim 1 wherein the first material is tungsten and the second material is aluminum.

13. An ultrasonic medical device comprising a one-half wave resonant transducer coupled with a one-half wave ultrasonic waveguide, wherein the one-half wave ultrasonic waveguide comprises a hot isostatically pressed component body comprising a one-quarter wave first material and a one-quarter wave second material, the first material having an acoustic impedance of $40 \times 10^5$ (gm/cm$^2$ sec) or more, and the second material having an acoustic impedance of less than $40 \times 10^5$ (gm/cm$^2$ sec), wherein the entire hot isostatically pressed component body has a substantially uniform cross-section.

14. The ultrasonic medical device as set forth in claim 13 wherein the first material has an acoustic impedance of greater than about $100 \times 10^5$ (gm/cm$^2$ sec).

15. The ultrasonic medical device as set forth in claim 13 wherein the second material has an acoustic impedance of less than $25 \times 10^5$ (gm/cm$^2$ sec).

16. The ultrasonic medical device as set forth in claim 13 wherein the first material is selected from the group consisting of copper, gold, iron, molybdenum, (nickel-copper alloy), nickel, platinum, steel, stainless steel, tungsten, and uranium.

17. The ultrasonic medical device as set forth in claim 13 wherein the first material is tungsten.

18. The ultrasonic medical device as set forth in claim 13 wherein the second material is selected from the group consisting of aluminum, beryllium, brass, cadmium, lead, magnesium, mercury, silver, tin, titanium, and zinc.

19. The ultrasonic medical device as set forth in claim 13 wherein the second material is aluminum.

* * * * *